(12) United States Patent
Lee et al.

(10) Patent No.: US 11,918,531 B2
(45) Date of Patent: Mar. 5, 2024

(54) THERMOTHERAPY DEVICE

(71) Applicant: CERAGEM CO., LTD., Cheonan-si (KR)

(72) Inventors: Dong Myoung Lee, Cheonan-si (KR); Sang Min Lee, Seoul (KR); Ho Sang Yu, Cheonan-si (KR); Ji Hoon Park, Cheonan-si (KR); Sang Ui Choi, Seoul (KR)

(73) Assignee: Ceragem Co., Ltd., Cheonan-si (KR)

( * ) Notice: Subject to any disclaimer, the term of this patent is extended or adjusted under 35 U.S.C. 154(b) by 194 days.

(21) Appl. No.: 16/802,486

(22) Filed: Feb. 26, 2020

(65) Prior Publication Data
US 2020/0214929 A1 Jul. 9, 2020

Related U.S. Application Data

(63) Continuation of application No. 14/783,716, filed as application No. PCT/KR2014/003093 on Apr. 9, 2014, now Pat. No. 10,610,443.

(30) Foreign Application Priority Data

Apr. 9, 2013 (KR) ........................ 10-2013-0038882
Apr. 9, 2013 (KR) ........................ 10-2013-0038883

(51) Int. Cl.
*A61H 15/00* (2006.01)
*A61F 7/00* (2006.01)
(Continued)

(52) U.S. Cl.
CPC ........... *A61H 15/0078* (2013.01); *A61F 7/00* (2013.01); *A61F 7/032* (2013.01); *A61H 15/00* (2013.01);
(Continued)

(58) Field of Classification Search
CPC ........... A47C 4/52; A47C 17/82; A47C 17/70; A47C 19/12; A47C 19/122; A47C 19/124;
(Continued)

(56) References Cited

U.S. PATENT DOCUMENTS 1,541,105 A * 6/1925 Broome ............... A47C 19/122
5/151
2,884,923 A 5/1959 Buffalow
(Continued)

FOREIGN PATENT DOCUMENTS

CN 87200357 U * 1/1987 ............. A47C 17/00
CN 2034804 U * 5/1988 ............. A47C 17/02
(Continued)

OTHER PUBLICATIONS

English translation for CN 201197797, espacenet.com, translated on Feb. 25, 2022.*
(Continued)

*Primary Examiner* — Tu A Vo
(74) *Attorney, Agent, or Firm* — Knobbe Martens Olson & Bear LLP (57) ABSTRACT

Provided is a thermotherapy device, which includes a first housing (10), a second housing (20) disposed under the first housing (10), a transfer plate (30), at both sides of which transfer rollers (31) are provided, and a pair of guide rails (40) that is provided to the second housing (20) and on which the respective transfer rollers (31) of the transfer plate (30) are placed. The pair of guide rails (40) are integrally molded when the second housing (20) is injection-molded. Thus, since the guide rails on which the transfer rollers of the transfer plate travel are integrally molded when the second housing is injection-molded, inefficiency caused by mounting separate rails as in the related art is removed, and thereby (Continued)

assemblability, productivity, and economic efficiency of the thermotherapy device can be improved.

15 Claims, 8 Drawing Sheets

(51) Int. Cl.
*A61F 7/03* (2006.01)
*A61H 15/02* (2006.01)

(52) U.S. Cl.
CPC ..... *A61H 15/02* (2013.01); *A61H 2015/0014* (2013.01); *A61H 2201/0142* (2013.01); *A61H 2201/0157* (2013.01); *A61H 2201/0161* (2013.01); *A61H 2201/0207* (2013.01); *A61H 2201/1215* (2013.01); *A61H 2201/1669* (2013.01); *A61H 2201/5066* (2013.01)

(58) Field of Classification Search
CPC .......... A47C 19/126; A61H 2015/0028; A61H 2015/0035; A61H 2015/0042; A61H 2015/005; A61H 2015/0057; A61H 2015/0064; A61H 2015/0071; A61H 15/0078; A61H 15/02; A61H 2201/0142; A61H 2201/0161; A61H 2201/5066; A61H 2201/1669; A61H 2201/1215; A61H 2201/0207; A61H 2201/0157; A61H 2015/0014; A61H 15/00; A61H 2015/0007; A61H 2015/0021; A61H 7/00; A61H 7/001; A61H 7/002; A61H 7/004; A61H 7/007; A61H 7/008; A61H 2007/009; A61F 7/00; A61F 7/032; Y10T 292/0913; Y10T 292/0917; Y10T 292/0871; Y10T 292/108; Y10T 292/092; Y10T 292/216; Y10T 24/1418; Y10S 292/31; Y10S 292/49; Y10S 292/63; E05C 19/14; E05C 19/145; E05B 15/0086; A47D 7/002; A45C 13/1084
See application file for complete search history.

(56) References Cited

U.S. PATENT DOCUMENTS

| | | | | |
|---|---|---|---|---|
| 2,948,905 A * | 8/1960 | Sevcik | ................ | A47C 19/122 |
| | | | | 5/152 |
| 3,089,151 A * | 5/1963 | Sevcik | ................ | A47C 19/122 |
| | | | | 5/149 |
| 3,286,709 A * | 11/1966 | Hoyer | ................ | A61H 1/024 |
| | | | | 601/24 |
| 4,327,713 A * | 5/1982 | Okazaki | ............ | A61H 23/0254 |
| | | | | 601/134 |
| 4,458,675 A * | 7/1984 | Nakao | ................ | A61H 15/0078 |
| | | | | 601/102 |
| 4,574,786 A | 3/1986 | Hashimoto et al. | | |
| 4,656,998 A * | 4/1987 | Masuda | ................ | A61H 15/0078 |
| | | | | 601/116 |
| 4,662,362 A * | 5/1987 | Masuda | ................ | A61H 1/00 |
| | | | | 601/102 |
| 4,712,538 A * | 12/1987 | Hardie | ................ | A61H 33/06 |
| | | | | 601/16 |
| 4,947,833 A * | 8/1990 | Yamasaki | .......... | A61H 15/0078 |
| | | | | 601/102 |
| 5,038,757 A * | 8/1991 | Yamasaki | ................ | A61G 7/05 |
| | | | | 601/102 |
| 5,101,809 A * | 4/1992 | Daffer | ................ | A61M 35/00 |
| | | | | 601/16 |
| 5,103,808 A * | 4/1992 | Lams | ................ | A61H 1/008 |
| | | | | 601/134 |
| 5,755,677 A | 5/1998 | Masuda et al. | | |
| 5,891,186 A * | 4/1999 | Daffer | ................ | A61H 23/02 |
| | | | | 600/27 |
| 6,056,708 A | 5/2000 | Sayama et al. | | |
| 6,243,609 B1 * | 6/2001 | Lee | ................ | A61H 39/06 |
| | | | | 607/90 |
| 6,283,929 B1 | 9/2001 | Mjehovic | | |
| 6,409,689 B1 * | 6/2002 | Chen | ................ | A61H 15/0078 |
| | | | | 601/99 |
| 6,542,779 B1 * | 4/2003 | Lee | ................ | A61F 7/02 |
| | | | | 607/90 |
| 6,606,520 B1 | 8/2003 | Lee | | |
| 6,814,710 B1 | 11/2004 | Dehli | | |
| 8,016,089 B1 * | 9/2011 | McNichols | ............. | A45C 5/14 |
| | | | | 190/18 R |
| 2001/0011160 A1 | 8/2001 | Oguma et al. | | |
| 2002/0003360 A1 * | 1/2002 | Maier | ................ | A47C 9/002 |
| | | | | 297/35 |
| 2002/0082533 A1 * | 6/2002 | Dehli | ................ | A61H 15/0078 |
| | | | | 601/97 |
| 2002/0193713 A1 * | 12/2002 | Lee | ................ | A61H 15/0078 |
| | | | | 601/99 |
| 2004/0015217 A1 * | 1/2004 | Lofgren | ................ | A61H 9/00 |
| | | | | 607/96 |
| 2004/0049842 A1 | 3/2004 | Prehodka | | |
| 2005/0015126 A1 * | 1/2005 | Doo | ................ | A61H 15/02 |
| | | | | 607/108 |
| 2005/0065580 A1 * | 3/2005 | Choi | ................ | A61F 7/00 |
| | | | | 601/19 |
| 2005/0226449 A1 * | 10/2005 | Young | ................ | A61H 23/0236 |
| | | | | 381/301 |
| 2005/0245851 A1 | 11/2005 | Ferber et al. | | |
| 2007/0239237 A1 * | 10/2007 | Choi | ................ | A61F 7/02 |
| | | | | 607/96 |
| 2008/0177212 A1 * | 7/2008 | Kim | ................ | A61H 15/00 |
| | | | | 602/33 |
| 2011/0068588 A1 * | 3/2011 | Kopylov | ................ | E05C 19/14 |
| | | | | 292/200 |

FOREIGN PATENT DOCUMENTS

| | | | |
|---|---|---|---|
| CN | 1714768 A | | 1/2006 |
| CN | 201197797 Y | * | 2/2009 |
| CN | 302416731 S | | 4/2013 |
| EP | 1208834 A1 | | 5/2002 |
| JP | 3141288 U | | 5/2008 |
| KR | 1997-0002202 B1 | | 2/1997 |
| KR | 10-0253880 B1 | | 4/2000 |
| KR | 200161704 Y1 | * | 6/2000 |
| KR | 10-2002-0025851 A | | 4/2002 |
| KR | 10-2002-0078516 A | | 10/2002 |
| KR | 10-2002-0085703 A | | 11/2002 |
| KR | 20-0314131 Y1 | | 5/2003 |
| KR | 10-2003-0064459 A | | 8/2003 |
| KR | 20-0340146 Y1 | | 1/2004 |
| KR | 10-0742781 B1 | | 7/2007 |
| TW | 510796 B | * | 3/2002 |

OTHER PUBLICATIONS

English translation for CN 87200357, machine translated by Search Clarivate Analytics, translated on Oct. 4, 2022.*
English translation for CN 2034804, machine translated by Search Clarivate Analytics, translated on Oct. 4, 2022.*
English translation for KR 200161704, machine translated by Search Clarivate Analytics, translated on Feb. 24, 2023.*
English translation for TW 510796, machine translated by Search Clarivate Analytics, translated on Feb. 25, 2023.*
International Search Report dated Jun. 13, 2014 of PCT/KR2014/003093 which is the parent application and its English translation—6 pages.
Office Action dated Jun. 12, 2014 of corresponding Korean Patent Application No. 10-2013-0038883—4 pages.

* cited by examiner

THERMOTHERAPY DEVICE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

TECHNICAL FIELD

The present invention relates to a thermotherapy device in which guide rails on which transfer rollers of a transfer plate travel are integrally molded when a second housing is injection-molded, thereby removing inefficiency caused by mounting separate rails as in the related art, and thus assemblability, productivity, and economic efficiency of the thermotherapy device can be improved.

BACKGROUND ART

As a conventional thermotherapy device, a "massage device for balanced physical exercise" is disclosed in Korean Examined Patent Application Publication No. 1997-0002202 (published on Feb. 25, 1997, and referred to as "first related art").

The first related art includes a housing frame, a mat detachably located on the housing frame, a pair of first guide rails installed in parallel in the housing frame in a lengthwise direction, a first movable plate disposed on the guide rails in a bridge shape and installed so as to be movable along the guide rails, a vibrating means elastically installed on the first movable plate and vibrating in a vertical direction, and a moving means reciprocating the first movable plate.

According to the first related art, various functions such as massage, acupressure, and vibration are provided in a bed-shaped main body, thereby providing valuable aid in satisfactorily relieving bone abnormality and muscular fatigue and maintaining a balanced human body.

However, the first related art is configured so that the guide rails are separately manufactured and disposed in the housing frame. As such, work for installing the guide rails in the housing frame is additionally required. Further, since the guide rails are separately manufactured, a cost required to manufacture the guide rails should be additionally paid.

Furthermore, as another conventional massage device, a "massage apparatus for whole body" is disclosed in Korean Patent No. 10-0253880 (granted on Jan. 27, 2000, and referred to as "second related art").

The second related art is configured so that a rodless cylinder is disposed at an upper side of an inner reservoir of a bed in a lengthwise direction of the bed, a sprinkler that can ride and travel on the rodless cylinder is disposed at a side of the bed, a chain is drawn from both sides of the rodless cylinder and is tied to front and rear ends of the sprinkler, and a water pipe is connected to and communicates with the rodless cylinder via a typical solenoid valve opened/closed selectively so that the sprinkler is reciprocated with energy of high-pressure water.

However, the second related art has a problem in that, since a length or size of the bed cannot be adjusted, transportation or transfer of the apparatus is inconvenient, and storage or carrying of the apparatus is difficult. When the apparatus is stored when not used, there is a problem in that the apparatus occupies a wide area to reduce space efficiency.

DISCLOSURE

Technical Problem

The present invention is directed to a thermotherapy device in which, since guide rails on which transfer rollers of a transfer plate travel are integrally molded when a second housing is injection-molded, inefficiency caused by mounting separate rails as in the related art is removed, and thereby assemblability, productivity, and economic efficiency of the thermotherapy device can be improved.

The present invention is directed to a thermotherapy device in which an upper surface of each guide rail is formed as an inclined slide part, each transfer roller placed on each slide part is formed in an inclined shape so as to correspond to each slide part, and a contact surface between each slide part and each transfer roller is inclined, so that, during traveling, the transfer rollers can be prevented from being fluctuated and separated so as to improve stability of the transfer rollers.

The present invention is directed to a thermotherapy device in which a limit switch is provided to a transfer plate and provides an automatic direction switching function when the transfer plate reaches a leading end or a trailing end of a traveling path, so that operation performance of the thermotherapy device can be improved.

The present invention is directed to a thermotherapy device in which a holder for housing a remote controller for remote control of the thermotherapy device is provided to a housing so as to easily store the remote controller, and a magnet is provided to the remote controller or holder so as to be able to attach or detach the remote controller and to improve the convenience of use.

The present invention is directed to a thermotherapy device in which a housing and a cover member are hinged by a coupling member, and the cover member is unfolded when the thermotherapy device is used and is folded when the thermotherapy device is not used, so that a size of the thermotherapy device can be remarkably reduced, the thermotherapy device can be easily carried and stored when not used, the convenience of use can be increased by improving mobility, and the cover member can be easily folded and/or unfolded to increase the convenience of use.

The present invention is directed to a thermotherapy device in which a cover member is formed to be thinner than a body in order to reduce a thickness of the thermotherapy device, and is separated from a floor due to a thickness difference from a housing when unfolded and used, and a supporting means is provided to prevent the cover member from leaning or sagging, and supports the cover member so as to be able to horizontally maintain the cover member when the thermotherapy device is used and to realize a stable support structure.

Technical Solution

According to an aspect of the present invention, there is provided a thermotherapy device, which includes a first housing; a second housing disposed under the first housing; a transfer plate, at both sides of which transfer rollers are provided; and a pair of guide rails that is provided to the second housing and on which the respective transfer rollers of the transfer plate are placed. The pair of guide rails are integrally molded when the second housing is injection-molded.

The pair of guide rails may further include slide parts, which are inclined in an inward direction, on upper surfaces thereof.

The transfer rollers of the transfer plate may further include contact parts whose outer circumferential surfaces are inclined in the inward direction so as to correspond to the slide parts of the guide rails.

The first housing may further include anti-separation members that are disposed above the transfer rollers and prevent the transfer rollers from being separated from the guide rails while the transfer rollers are traveling.

Each of the transfer rollers may further include an annular guide flange on an inner lateral surface thereof which protrudes in a radial outward direction.

According to another aspect of the present invention, there is provided a thermotherapy device, which includes: a first housing; a second housing disposed under the first housing; a transfer plate, at both sides of which transfer rollers are provided; a pair of guide rails that is provided to the second housing and on which the respective transfer rollers of the transfer plate are placed; and a limit switch provided in the front and/or rear of the transfer plate.

According to another aspect of the present invention, there is provided a thermotherapy device, which includes: a first housing; a second housing disposed under the first housing; a transfer plate, at both sides of which transfer rollers are provided; a pair of guide rails that is provided to the second housing and on which the respective transfer rollers of the transfer plate are placed; a remote controller performing remote control; and a holder that is formed in the first housing and/or the second housing and in which the remote controller is housed.

The holder and/or the remote controller may further include a detachable member that attaches or detaches the remote controller.

Advantageous Effects

In the thermotherapy device according to the present invention, since guide rails on which transfer rollers of a transfer plate travel are integrally molded when a second housing is injection-molded, inefficiency caused by mounting separate rails as in the related art is removed, and thereby assemblability, productivity, and economic efficiency of the thermotherapy device can be improved.

In the present invention, an upper surface of each guide rail is formed as an inclined slide part, each transfer roller placed on each slide part is formed in an inclined shape so as to correspond to each slide part, and a contact surface between each slide part and each transfer roller is inclined, so that, during traveling, the transfer rollers can be prevented from being fluctuated and separated so as to improve stability of the transfer rollers.

In the present invention, a limit switch is provided to a transfer plate and provides an automatic direction switching function when the transfer plate reaches a leading end or a trailing end of a traveling path, so that operation performance of the thermotherapy device can be improved.

In the present invention, a holder for housing a remote controller for remote control of the thermotherapy device is provided to a housing so as to easily store the remote controller, and a magnet is provided to the remote controller or holder so as to be able to attach or detach the remote controller and to improve the convenience of use.

In the present invention, a housing and a cover member are hinged by a coupling member, and the cover member is unfolded when the thermotherapy device is used and is folded when the thermotherapy device is not used, so that a size of the thermotherapy device can be remarkably reduced, the thermotherapy device can be easily carried and stored when not used, the convenience of use can be increased by improving mobility, and the cover member can be easily folded and/or unfolded to increase the convenience of use.

In the present invention, a cover member is formed to be thinner than a body in order to reduce a thickness of the thermotherapy device, and is separated from a floor due to a thickness difference from a housing when unfolded and used, and a supporting means is provided to prevent the cover member from leaning or sagging, and supports the cover member so as to be able to horizontally maintain the cover member when the thermotherapy device is used and to realize a stable support structure.

In the present invention, a backing member of the supporting means is hinged to a cover member so as to be able to be turned. A receiving part is provided to the cover member, and the backing member is housed in the receiving part, so that the thermotherapy device can improve the convenience of use.

In addition, the present invention includes a locking means. When the thermotherapy device is stored, the hinged body and cover member are prevented from being unfolded by themselves. Further, a transfer member is provided, so that the thermotherapy device is easily handled when transported or carried.

DESCRIPTION OF DRAWINGS

The above and other objects, features, and advantages of the present invention will become more apparent to those of ordinary skill in the art by describing in detail exemplary embodiments thereof with reference to the accompanying drawings, in which.

EMBODIMENTS

A thermotherapy device according to exemplary embodiments of the present invention will be described in detail below with reference to the accompanying drawings.

Figure 1:
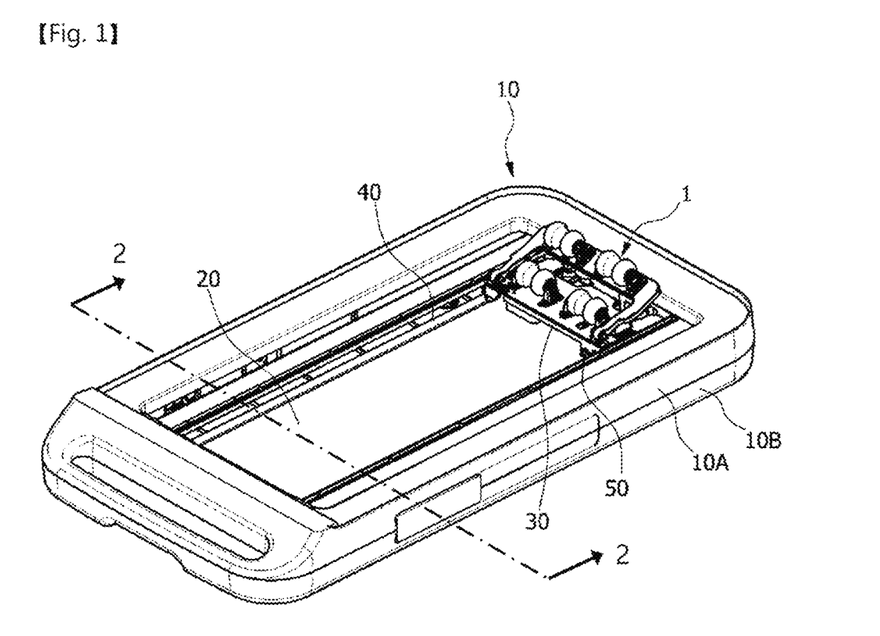
FIG. 1 is a perspective view showing a thermotherapy device according to an exemplary embodiment of the present invention.
Figure 2:
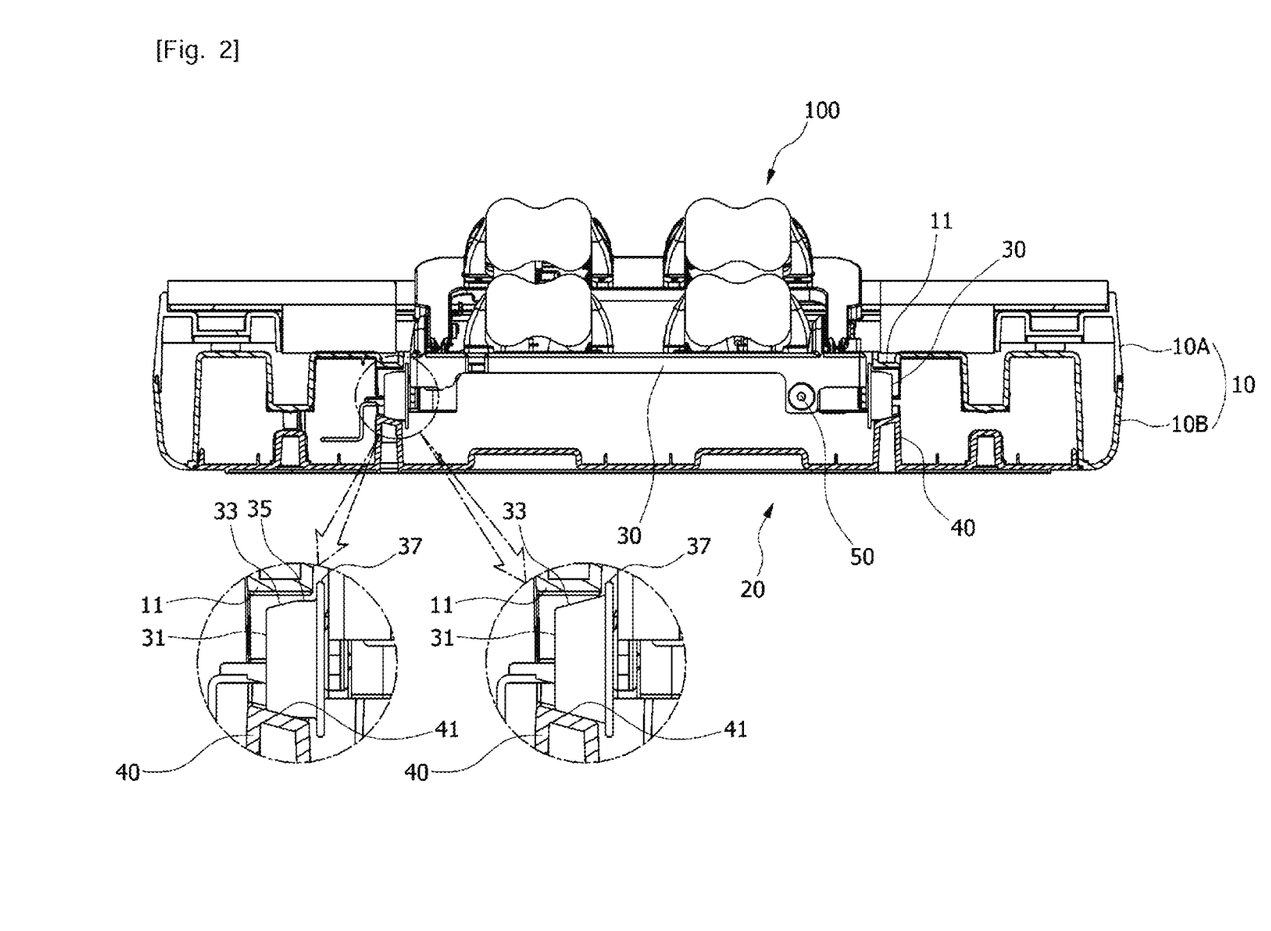
FIG. 2 is a cross-sectional view showing the thermotherapy device according to the exemplary embodiment of the present invention.
Figure 3:
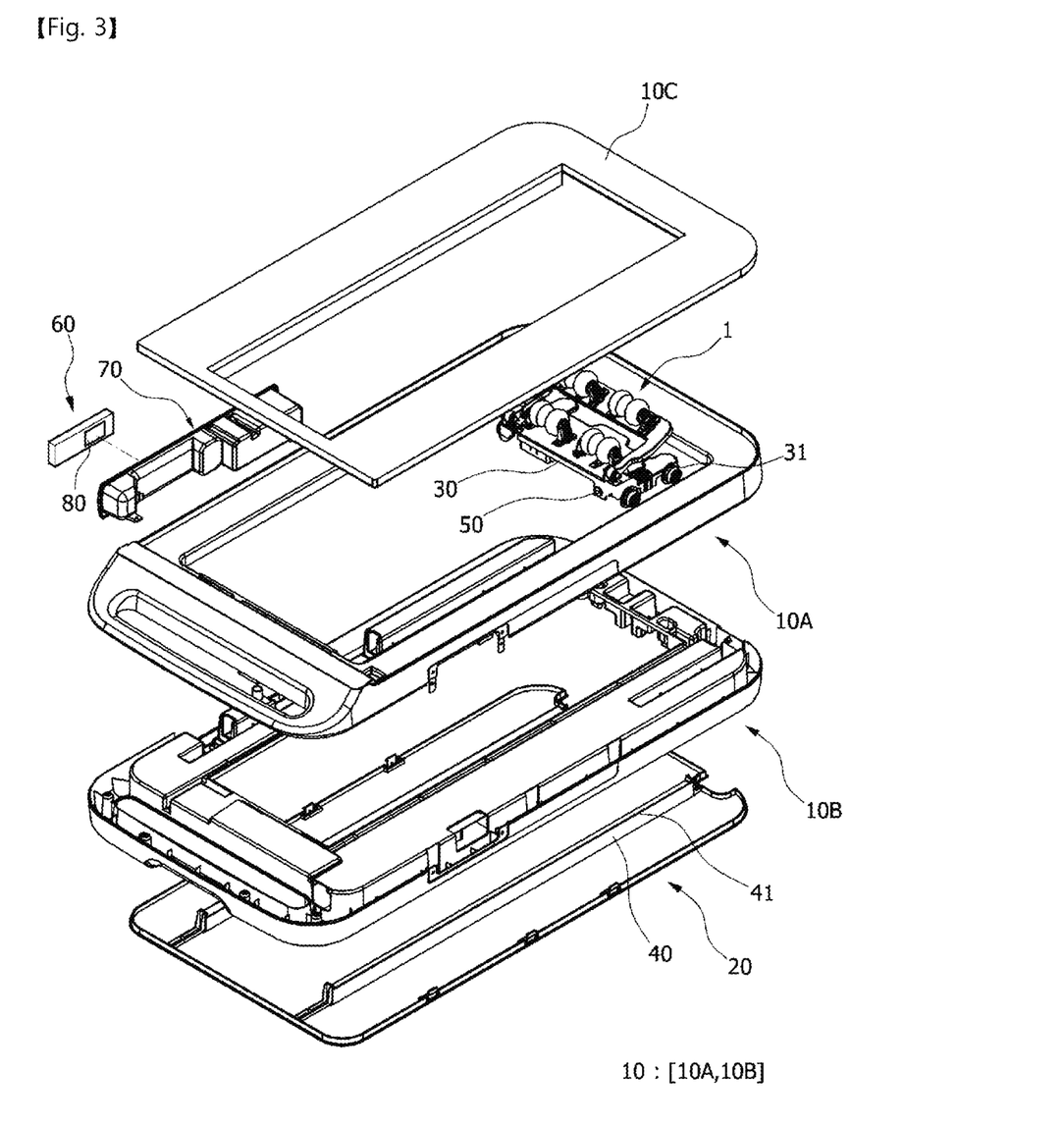
FIG. 3 is an exploded perspective view showing the thermotherapy device according to the exemplary embodiment of the present invention.

As shown in FIGS. 1 to 3, a thermotherapy device according to an exemplary embodiment of the present invention includes a first housing 10, a second housing 20, a transfer plate 30 equipped with transfer rollers 31 on both sides thereof, and a pair of guide rails 40 which are installed in the second housing 20 and on which the respective transfer rollers 31 are placed.

As shown in FIGS. 1 to 3, the first housing 10 and the second housing 20 are made by injection molding, and are disposed and coupled in a vertical direction.

In this case, an injection metal mold for molding the first and second housings 10 and 20 is made up of an upper metal mold and a lower metal mold, by which the respective housings are molded.

Here, the first housing 10 includes a middle housing 10B coupled to the second housing 20, an upper housing 10A coupled to the middle housing 10B, and a cover member 10C covering an upper edge of the upper housing 10A.

Further, a pair of guide rails 40 are provided on an upper surface of the second housing 20 and disposed in parallel in a forward/backward direction. The transfer rollers 31 installed on the transfer plate 30 are placed on the respective guide rails 40, so that the transfer plate 30 can travel.

The transfer plate 30 is mounted with a massage set 1. When power is supplied from a driving means, the transfer rollers 31 roll on the guide rails 40. Massage is conducted by forward and backward movements of the transfer plate 30.

Particularly, the guide rails 40 are integrally molded when the second housing 20 is injection-molded.

This structure can solve a problem that, since separate work for installing the rails should be performed when the rails are mounted as in the related art, workability is lowered productivity is reduced as well as a problem that a cost is required to manufacture separate rails, and thus economic efficiency is lowered, at a stroke.

In other words, since the guide rails 40 are integrally molded when the second housing 20 is injection-molded, the separate work for mounting the rails is not required, and the cost required to manufacture the rails can be cut. Thus, the economic efficiency can be enhanced.

Furthermore, in the present invention, the transfer rollers 31 rolling on the guide rails 40 may be prevented from being fluctuated or separated from the guide rails 40 so as to increase stability.

To this end, each guide rail 40 is provided with a slide part 41 on an upper surface thereof which is inclined in an inward and downward/upward direction, and each transfer roller 31 is provided with a contact part 33 inclined in an inward and upward/downward direction so as to correspond to the slide part 41.

That is, when the transfer rollers 31 are placed on the slide parts 41, each slide part 41 has the same slope as the contact part 33 of each transfer roller 31. As such, the transfer rollers 31 are subjected to a predetermined load (a load applied from the transfer plate 30 and a load that is applied from a user to the massage set 1 coming into contact with a body of the user) via the slopes thereof in an inward or outward direction.

Thus, even when an external force is applied to the transfer rollers 31 in a leftward/rightward direction or in an upward/downward direction, the transfer rollers 31 can be prevented from being fluctuated and separated by the slopes of the slide parts 41 and the contact parts 33, so that they can stably travel.

In the attached figure, the slide parts 41 and the contact parts 33 of the transfer rollers 31 are shown in such a way that the slopes thereof are inclined from outward to inward (first example). If necessary, the slopes of slide parts and the contact parts of the transfer rollers may be inclined from inward to outward (second example).

However, when the slopes of the slide parts 41 and the contact parts 33 of the transfer rollers 31 are formed as in the second example, a force is applied in opposite directions in which the transfer rollers 31 are widened. In this case, a tensile force is applied to joints between the transfer plate 30 and the transfer rollers 31, and thus the joints may be weakened. As such, the slopes of the slide parts 41 and the contact parts 33 of the transfer rollers 31 are preferably formed as in the first example in which they are inclined from outward to inward.

As shown in FIG. 2 (an upper enlarged view), the contact parts 33 of the transfer rollers 31 are preferably formed in an inclined shape on the whole.

Further, as another modification of the transfer roller, as shown in FIG. 2 (a lower enlarged view), in case of the first example, each transfer roller 31 is further provided with a flat part 35 to which the contact part 33 is connected, which is disposed at an outer side, and which is in contact with the slide part 41. Thereby, a frictional area between the transfer roller 31 and the slide part 41 is reduced so as to be able to reduce either power loss caused by friction or wear.

When this is applied to the second example, the flat part may be formed at an inner side so as to carry out the same function as described above.

Meanwhile, in the present invention, to prevent the fluctuation or separation of the transfer rollers 31, the first housing 10 is provided with anti-separation members 11 that are disposed above the guide rails 40 and are spaced apart from the guide rails 40 by a predetermined distance.

Each anti-separation member 11 protrudes downward and is disposed parallel with each guide rail 40 in a forward/backward direction. Since the transfer roller 31 is interposed between the guide rail 40 and the anti-separation member 11, the transfer rollers 31 are prevented from being fluctuated or separated in an upward direction by the anti-separation members 11.

In this case, to ensure smooth movement of the transfer rollers 31, the anti-separation members 11 may be maintained at a predetermined distance so as not to be in contact with the transfer rollers 31.

Further, as shown in FIG. 2, the anti-separation members 11 may be configured so that lower surfaces thereof are formed in a flat shape or in an inclined shape so as to correspond to the contact parts 33 of the transfer rollers 31. However, since it is preferable that the anti-separation members 11 are not in direct contact with the transfer rollers 31, the lower surfaces of the anti-separation members 11 may be not formed in the inclined shape.

Furthermore, each transfer roller 31 may be further provided with an annular guide flange 37 on an inner lateral surface thereof which protrudes in a radial outward direction. Thus, when the transfer rollers 31 move leftward/rightward, the guide flanges 37 are caught on inner walls of the guide rails 40 so as to prevent the transfer rollers 31 from being derailed from the slide parts 41. As a result, the stable travelling of the transfer rollers 31 is possible.

In this case, an outer diameter of each guide flange 37 is greater than a spaced distance between the guide rail 40 and the anti-separation member 11 so as to be able to be caught on the inner wall of the guide rail 40 as well as the anti-separation member 11 and thus to realize a more stable support structure.

Further, the transfer plate 30 is provided with a limit switch 50 in the front and/or rear thereof. When the transfer plate 30 arrives at a leading end or a trailing end of a travelling path thereof, the limit switch 50 comes into contact with the first or second housing so that a traveling direction of the transfer plate 30 can be automatically switched. Thereby, the apparatus can be smoothly operated.

In this case, the limit switch 50 may be installed in the front and/or rear of the transfer plate 30.

In addition, a remote controller 60 is provided so as to remotely control the thermotherapy device. The remote controller 60 is housed in a holder 70 provided in the first housing 10 and/or the second housing 20.

Thus, the holder 70 allows the remote controller 60 to be easily stored as well as to be always disposed at the thermotherapy device, and thus can improve the convenience of use.

In this case, the holder 70 of a box shape is mounted in the middle housing 10B and the upper housing 10A constituting the first housing 10. However, the holder 70 is to provide convenience for a user, and may be provided at an optimal place in which the convenience of use can be ensured.

Further, the holder 70 and/or the remote controller 60 are provided with a detachable member 80 for attaching or detaching the remote controller 60. The detachable member 80 may be an attached type such as a magnet or a Velcro, or a structure in or from which the remote controller 60 is fitted or extracted.

Here, when the detachable member 80 is the magnet or the Velcro, it may be provided for both the holder 70 and the remote controller 60. When the detachable member is the structure, it may be provided only inside the holder 70 or for both the holder 70 and the remote controller 60 so as to correspond to each other.

Hereinafter, as a thermotherapy device according to another exemplary embodiment of the present invention, a thermotherapy device configured in a foldable type will be described in greater detail with reference to the attached figures.

Figure 4:
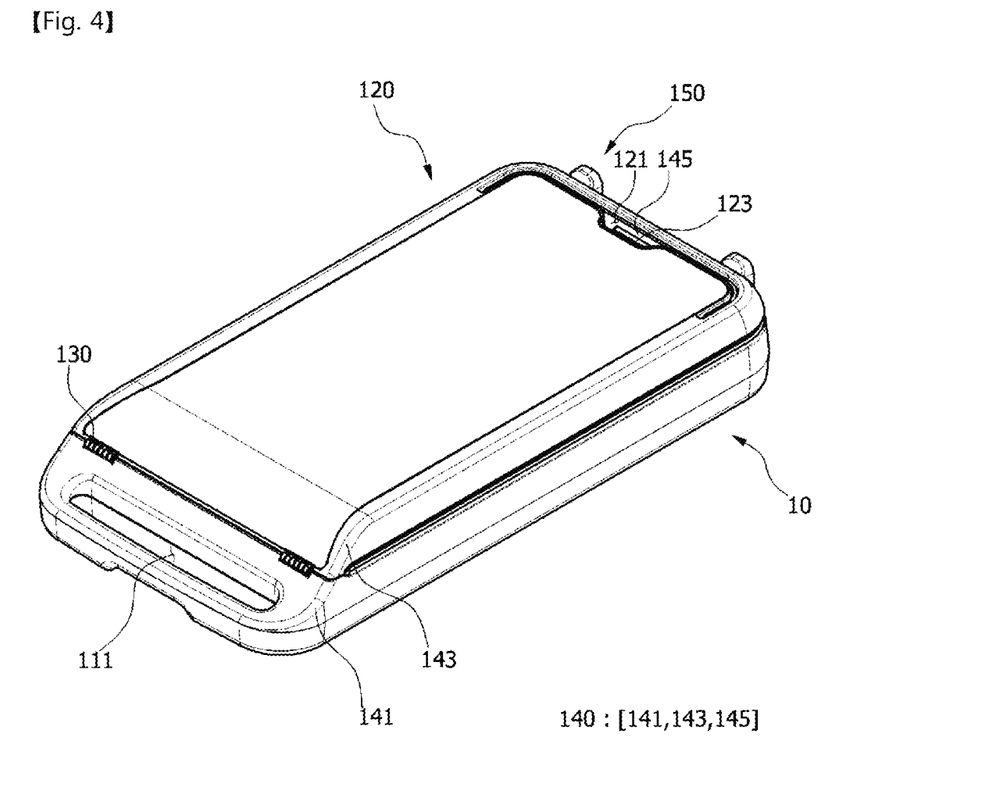
FIGS. 4 and 5 are perspective views showing a thermotherapy device according to another exemplary embodiment of the present invention.

First, a criterion of a direction used herein is defined with reference to FIG. 4. In a state in which a cover member 120 is folded back on a housing 100, a side at which a handle 111 is provided is defined as a "front" or a "leading end," and a side at which a locking means 150 is defined as a "rear" or a "trailing end."

Figure 5:
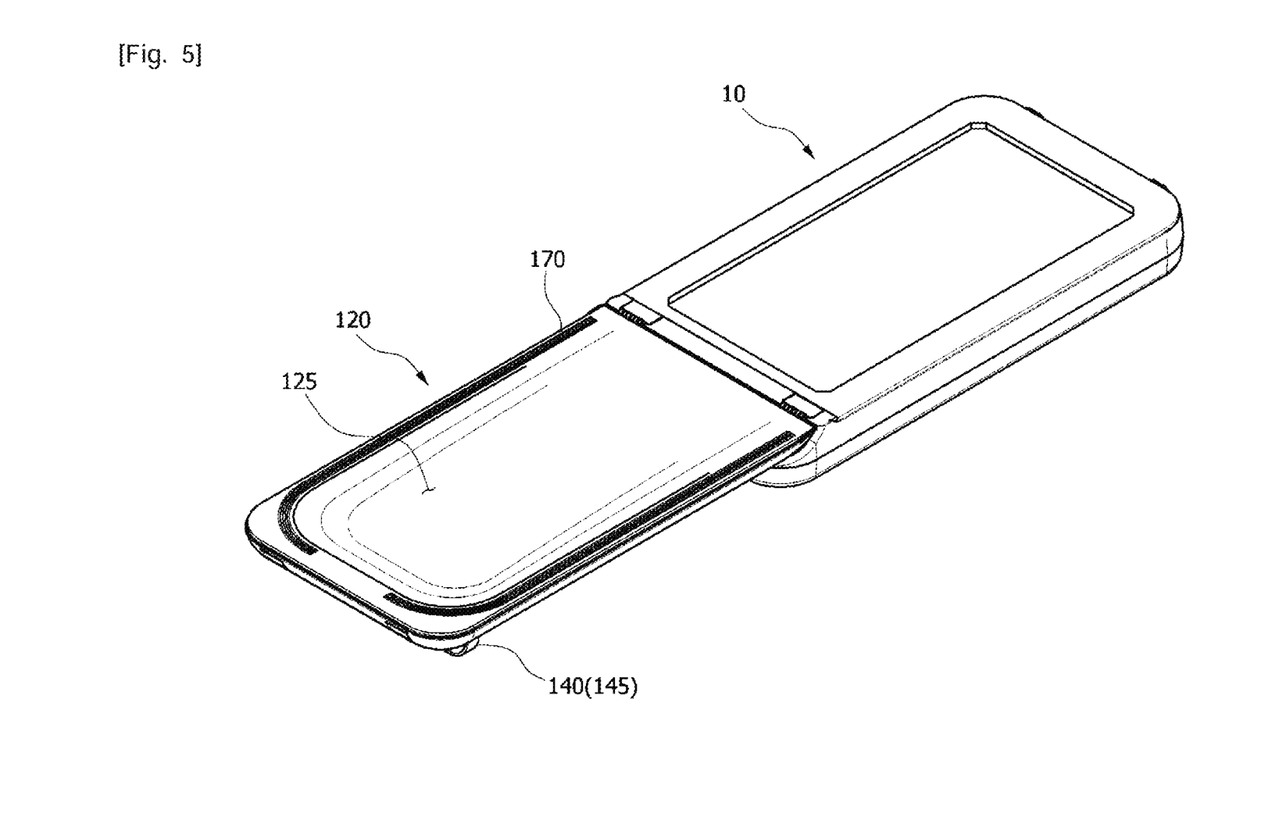
Figure 6:
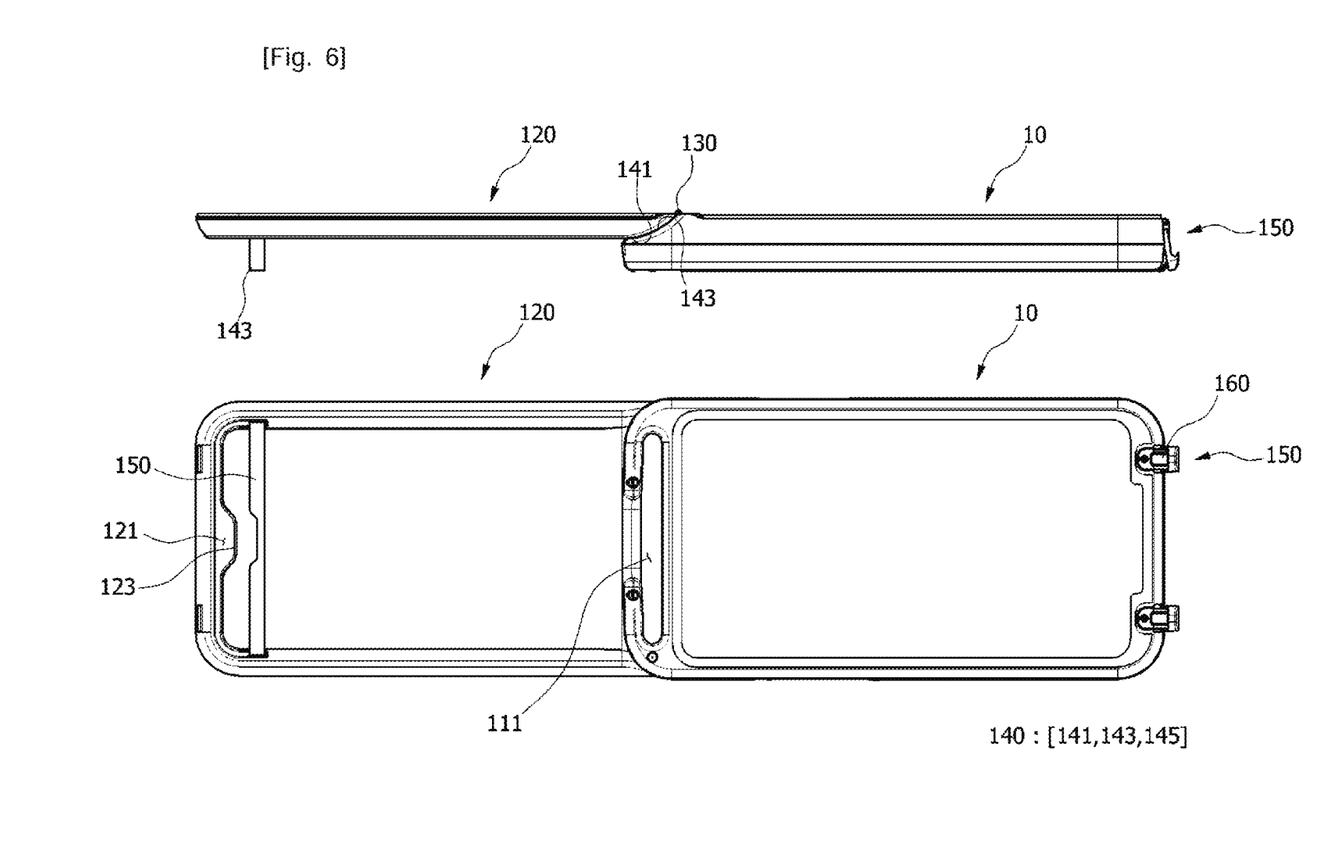
FIG. 6 is a side view and a bottom view showing the thermotherapy device of FIGS. 4 and 5.

As shown in FIGS. 4 to 6, a foldable thermotherapy device according to another exemplary embodiment of the present invention includes a housing 100, a cover member 120 opening/closing the housing 100, a coupling member 130 hinging the housing 100 and the cover member 120, and a supporting means 140 configured to horizontally maintain the cover member 120.

As shown in FIGS. 4 to 6, the housing 100 provides an installation space in which a massage set (not shown) and a driving means for transferring the massage set are mounted, and is connected to the cover member 120. When the cover member 120 is unfolded, the housing 100 functions as a bed in which a user can lie face up or down along with the cover member 120.

Further, similar to that shown in FIG. 1, the housing 100 includes a first housing 10 made up of an upper housing 10A and a lower housing 10B, and a second housing 20.

However, in FIGS. 4 to 7, the second housing forming the bottom of the thermotherapy device is not shown.

Thus, the housing described below is set to indicate the first housing of FIGS. 1 to 3.

As shown in FIGS. 4 to 6, the cover member 120 is configured so that a leading end thereof is hinged to a leading end of the housing 100 by the coupling member. Thus, the cover member 120 is configured in a folder type in which it can be unfolded when the thermotherapy device is used and be folded when the thermotherapy device is not used.

As shown in FIGS. 4 to 6, the leading end of the housing 100 is connected to the leading end of the cover member 120, and thus the coupling member 130 allows the cover member 120 to pivot around the coupling member 130, thereby allowing the cover member 120 to be unfolded or folded.

To this end, the coupling member 130 preferably employs a known component such as a hinge so as to be able to reduce a unit cost of a product.

The housing 100 of the thermotherapy device according to the present invention is manufactured so as to have a predetermined thickness to secure the installation space as described above.

In this case, to make the thermotherapy device slim, the thickness of the housing 100 may be formed so as to have a minimum thickness.

However, to obtain the slim thermotherapy device, the housing 100 encounters a limit in reducing its thickness due to the restrictions as described above. As such, a thickness of the cover member 120 may be considerably reduced so as to be able to make a product slim and lightweight.

Here, a thickness ratio of the housing 100 to the cover member 120 may be maintained within a range of 1:0.2 to 1:0.8.

Thus, when the cover member 120 is unfolded to use the thermotherapy device, the cover member 120 has a cantilever structure in which it is spaced apart from a floor by a predetermined height due to a thickness difference between the cover member 120 and the housing 100.

In this case, when a user lies face up or down in order to use the thermotherapy device, a trailing end of the cover member 120 leans or sags due to weight of the user, which incurs the inconvenience of use.

To prevent this, the supporting means 140 is provided so as to obtain a stable support structure when the cover member 120 is unfolded, so that it can prevent the leaning or sagging of the cover member 120.

The supporting means 140 includes first and second contact parts 141 and 143 supporting the leading end of the cover member 120, and a backing member 145 supporting the trailing end of the cover member 120.

First, the first contact part 141 of the supporting means 140 is formed at the leading end of the housing 100 in an upward curved shape, and the second contact part 143 is formed at the leading end of the cover member 120 in a downward curved shape so as to correspond to the first contact part 141.

Thus, when the cover member 120 is unfolded, the second contact part 143 comes into contact with the first contact part 141, thereby supporting the leading end of the cover member 120.

Next, the backing member 145 of the supporting means 140 has a square bracket shape, and both ends thereof are hinged to the trailing end of the cover member 120, thereby supporting the trailing end of the cover member 120.

In this case, the backing member 145 may be configured to have a height corresponding to the thickness difference between the housing 100 and the cover member 120, thereby compensating for the thickness difference between the housing 10 and the cover member 120.

The cover member 120 is provided with a receiving part 121 that houses the backing member 145. The receiving part 121 is shaped of a groove corresponding to a shape of the backing member 145.

Although not shown in the attached figure, the backing member of the supporting means can be installed in various shapes such as a shape in which two legs are separated, in addition to the square bracket shape.

The both ends of the backing member 145 are hinged to inner sides of both ends of the receiving part 121. When the cover member 120 is unfolded and used, the backing member 145 is extracted from the receiving part 121, comes into contact with a floor, and supports the trailing end of the cover member 120.

In contrast, when the cover member 120 is folded, the extracted backing member 145 is turned to enter the receiving part 121. It is preferable that, when the thermotherapy device is not used, the backing member 145 can be compactly housed so as not to be unnecessarily exposed.

Furthermore, the receiving part 121 is provided with a grasping recess 123 so as to allow the backing member 145 to be easily extracted. When the backing member 145 is extracted, the grasping recess 123 may increase the convenience of use by permitting access of a finger of a user.

As described above, when the cover member 120 is unfolded and used, the supporting means 140 can prevent the cover member 120 from leaning or sagging because the first and second contact parts 141 and 143 support the leading end of the cover member 120 and because the backing member 145 supports the trailing end of the cover member 120 from the floor.

Thereby, the stable support structure is realized so as to allow the cover member 120 to be horizontally maintained. Accordingly, when the thermotherapy device is used, the inconvenience of a user can be removed to improve the reliability of the thermotherapy device.

Figure 7:
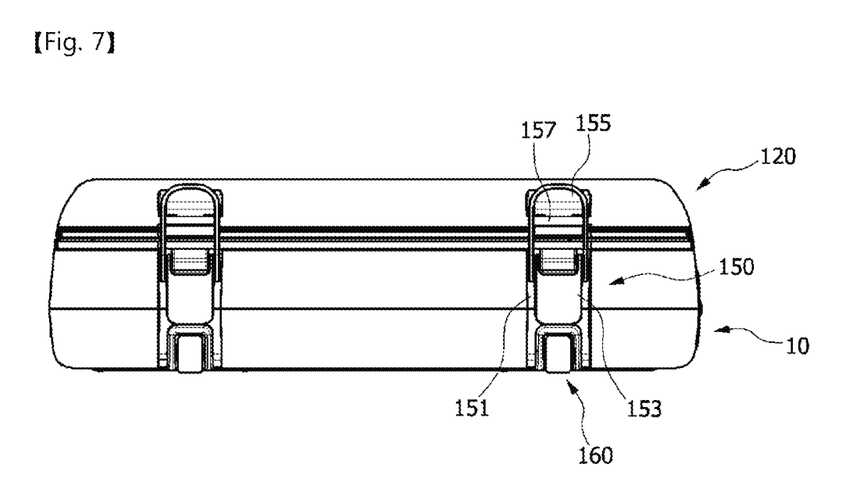
FIG. 7 is a front view showing the thermotherapy device of FIGS. 4 and 5.
Figure 8A:
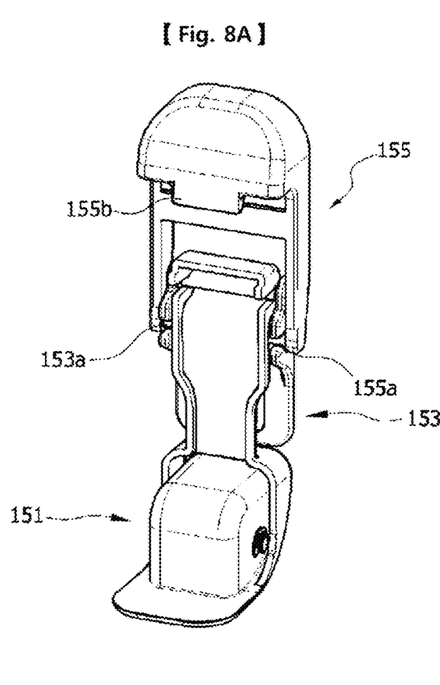
FIG. 8A and FIG. 8B show a locking means of the thermotherapy device according to embodiments of the present invention.
Figure 8B:
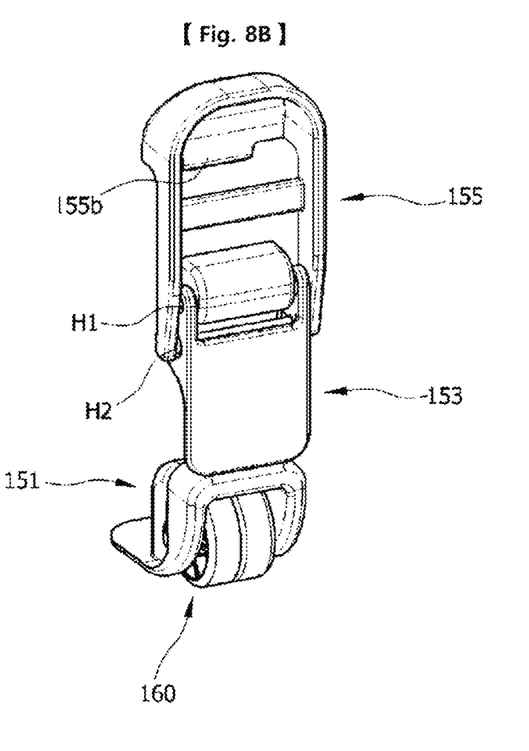

Furthermore, as shown in FIGS. 7, 8A and 8B, the thermotherapy device according to the present invention is provided with a locking means 150 coupled to the housing 100 and the cover member 120.

Since the housing 100 and the cover member 120 are hinged by the coupling member 130, when the thermotherapy device is stored, carried, or transported, and particularly when the thermotherapy device stands, the cover member 120 may be turned around and unfolded from the housing 100 by itself. This is preferably prevented so as to provide the convenience of use.

To this end, the locking means 150 includes a body 151 connected to the housing 100, an actuating member 153 hinged to the body 151, a hooking member 155 hinged to the actuating member 153, and a hooked slot 157 which is formed in the cover member 120 and into and from which the hooking member 155 is inserted and extracted.

The body 151 of the locking means 150 is fixedly installed on an outer surface of the trailing end of the housing 100 by a bolt or a pin, and the actuating member 153 is rotatably coupled to an upper end of the body 151 by a first hinge coupler H1.

The hooking member 155 is provided with a support rod 155a at a lower end thereof, and a rotary space is formed above the support rod 155a so that rotation of the actuating member 153 is possible.

Further, the actuating member 153 is provided with fitting recesses 153a into which the support rod 155a is fitted so that the rotation of the actuating member 153 is possible. A second hinge coupler H2 is formed by the support rod and the fitting recesses.

In this case, in a state in which the thermotherapy device is locked, the second hinge coupler H2 is located below the first hinge coupler H1.

Further, the hooking member 155 is provided with a hooking protrusion 155b at an upper portion thereof which protrudes downward or in a hook shape. The hooking protrusion 155b is inserted into and/or extracted from the hooked slot 157, thereby performing a locking function.

As for an unlocking operation of the locking means 150, first, when the actuating member 153 is pulled back upward in order to unlock the locked thermotherapy device, the actuating member 153 is turned upward.

Thus, the second hinge coupler H2 moves upward. Thereby, the hooking member 155 moves upward, and the hooking protrusion 155b is extracted from the hooked slot 157, so that the locked state is released.

In contrast, as for an locking operation caused by the locking means 150, when the hooking protrusion 155b of the hooking member 155 is located above the hooked slot 157, the second hinge coupler H2 is located above the first hinge coupler H1.

In this state, when the actuating member 153 is rotated downward, the second hinge coupler H2 moves downward. Further, the hooking member 155 also moves downward, and the hooking protrusion 155b is inserted into the hooked slot 157, so that the unlocked state is switched into the locked state.

As described above, the locking means 150 employs a clamp type, and ensures the convenience of use. If necessary, the locking means 150 can employ various types in order to lock the housing 100 and the cover member 120. As such, the locking means 150 as described above is merely one of embodied various examples.

Further, as shown in FIGS. 7, 8A and 8B, the thermotherapy device according to the present invention is provided with a transfer member 160 in order to provide convenience when transported.

The transfer member 160 is made up of a transfer roller connected to a lower portion of the body 151 of the locking means 150.

In this case, the transfer member 160 is installed on the body 151 of the locking means 150, and is located at the trailing end of the thermotherapy device.

When a user grasps the handle 111 to transport or carry the thermotherapy device in which the handle 111 is provided to the leading end of the housing 100, the thermotherapy device is raised, and the trailing end thereof comes into contact with a floor. As such, the transfer member 160 is preferably located at the trailing end of the thermotherapy device.

Further, the transfer member 160 is preferably provided to the locking means 150.

When the transfer member 160 is mounted on the housing 100 or the cover member 120, the transfer member 160 not only damages the housing 100 or the cover member 120 but also spoils the beauty of the housing 100 or the cover member 120. For this reason, when the transfer member 160 is installed on the body 151 of the locking means 150 fixed to the housing 100, the transfer member 160 may prevent damage to the housing 100 or the cover member 120, and maintain the beauty of the housing 100 or the cover member 120.

However, the transfer member 160 may be manufactured in various shapes such as a wheel or a caster, in addition to the roller.

Meanwhile, as shown in FIG. 7, the thermotherapy device according to the present invention is configured so that a recess 125 is formed in an inner surface of the cover member 120 so as to prevent interference between the massage set and the cover member 120.

The massage set (not shown) provided in the housing 100 should be disposed in an upward protruding state in order to realize a massage or acupressure function. As such, when the cover member 120 is configured in a flat plate shape and when the housing 100 is covered with the cover member 120, an upper end of the massage set comes into contact with the inner surface of the cover member 120 and the housing 100 is not completely covered with the cover member 120. To solve this problem, the recess 125 is formed in the inner surface of the cover member 120.

Thus, the recess 125 causes the cover member 120 to have a cap shape. When the cover member 120 covers the housing 100, the massage set is housed in an internal space of the cover member 120 which is formed by the recess 125, so that the interference between the cover member 120 and the massage set can be prevented, and thus the cover member 120 can completely cover the housing 100.

Furthermore, the thermotherapy device according to the present invention is provided with a damping member 170 formed on the housing 100 and/or the cover member 120.

As shown in FIG. 5, the damping member 170 may be mounted on an edge of the inner surface of the cover member 120 or an edge of the housing 100. If necessary, the damping member 170 may be mounted on the cover member 120 and the housing 100 at mutually corresponding positions.

The damping member 170 is formed of an elastic material such as rubber, silicone, or an elastomer. When the cover member 120 is turned to cover the housing 100, the damping member 170 absorbs a shock occurring when the cover member 120 collides with the housing 100 so as to be able to reduce a damage and noise occurring in the event of the collision and thus to improve quality of the thermotherapy device.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

The invention claimed is:

1. A massage device comprising:
a housing defining a massage set space, the housing comprising a first body support surface that faces upward and configured to support a user's body, the housing further comprising a first opposite surface facing away from the first body support surface and facing downward;
a massage set disposed in the massage set space;
a cover connected to the housing, the cover comprising a second body support surface configured to support the user's body, and the cover further comprising a second opposite surface facing away from the second body support surface; and
a coupler connecting the housing and the cover and configured to allow the cover to be folded and unfolded about the coupler,
wherein the second body support surface of the cover faces upward and the second opposite surface faces downward while the cover is in an unfolded position,
wherein the housing and the cover are configured to support the user's body placed on the first body support surface of the housing and the second body support surface of the cover while the cover is in the unfolded position,
wherein the cover is configured to cover the first body support surface of the housing while the cover is in a folded position such that the second body support surface of the cover faces the first body support surface of the housing and further such that the first opposite surface faces away from the second opposite surface and faces upward,
wherein the housing comprises a first contact surface facing upward and configured to support the cover while the cover is in the unfolded position,
wherein the cover comprises a second contact surface facing downward and configured to be in contact with and supported by the first contact surface of the housing while the cover is in the unfolded position,
wherein, while the cover is in the unfolded position, the first contact surface of the housing is disposed under the second contact surface of the cover to horizontally maintain the cover, and
wherein the first contact surface extends from the first body support surface, and the second contact surface extends from the second opposite surface.

2. The massage device of claim 1, further comprising a backing support configured to support and hingedly connected to the cover that comprises a receiving recess configured to house the backing support when the backing support is unfolded.

3. The massage device of claim 2, wherein the backing support, the first contact surface and the second contact surface are configured to support the cover such that the cover is prevented from sagging when the cover is in the unfolded position.

4. The massage device of claim 1, further comprising a locking latch that is provided to the housing and the cover and configured to allow mutual locking or unlocking of the housing and the cover.

5. The massage device of claim 4, wherein the locking latch includes:
a body connected to the housing;
an actuator hinged to the body;
a hook hinged to the actuator; and
a hooked slot which is formed in the cover such that the hook is inserted into and extracted from the hooked slot.

6. The massage device of claim 4, wherein the locking latch further includes at least one of a wheel or a caster for providing convenience of movement.

7. The massage device of claim 1, wherein the cover further includes an inner surface and a recess formed in the inner surface in order to prevent interference with the massage set disposed inside the housing when the housing is covered with the cover.

8. The massage device of claim 1, further comprising a damper formed on the housing and/or the cover.

9. The massage device of claim 1, wherein the housing and the cover have a thickness ratio of 1:0.2 to 1:0.8.

10. The massage device of claim 1, wherein the first contact surface is concavely curved and the second contact surface is convexly curved.

11. The massage device of claim 1, wherein the coupler is configured to hingedly connect the cover and the housing such that the cover is configured to pivot with respect to the housing about the coupler.

12. The massage device of claim 1, wherein the cover comprises an end portion where the coupler is connected, and the second contact surface is located at the end portion.

13. The massage device of claim 1, wherein the first contact surface is concavely curved and the second contact surface is convexly curved.

14. The massage device of claim 1, wherein the coupler is disposed between the first contact surface and the first body support surface when viewed toward the first body support surface.

15. The massage device of claim 1, wherein, when the cover is in the unfolded position, the second body support surface faces upward and the second contact surface faces downward while the first body support surface and the first contact surface face upward.

* * * * *